US012362066B2

(12) United States Patent
Valles Leon

(10) Patent No.: US 12,362,066 B2
(45) Date of Patent: Jul. 15, 2025

(54) TELEHEALTH INTERACTION TRACKING SYSTEM AND METHOD

(71) Applicant: MDLIVE, Inc., Miramar, FL (US)

(72) Inventor: Nakort E. Valles Leon, Weston, FL (US)

(73) Assignee: MDLive, Inc., Miramar, FL (US)

( * ) Notice: Subject to any disclaimer, the term of this patent is extended or adjusted under 35 U.S.C. 154(b) by 346 days.

(21) Appl. No.: 17/486,309

(22) Filed: Sep. 27, 2021

(65) Prior Publication Data
US 2023/0098614 A1 Mar. 30, 2023

(51) Int. Cl.
| | | |
|---|---|---|
| *G16H 40/67* | (2018.01) | |
| *G06Q 20/12* | (2012.01) | |
| *G06Q 40/08* | (2012.01) | |
| *G16H 20/13* | (2018.01) | |
| *G16H 40/20* | (2018.01) | |
| *G16H 70/20* | (2018.01) | |
| *H04L 67/12* | (2022.01) | |
| *H04L 67/50* | (2022.01) | |

(52) U.S. Cl.
CPC .......... *G16H 40/67* (2018.01); *G06Q 20/127* (2013.01); *G06Q 40/08* (2013.01); *G16H 20/13* (2018.01); *G16H 40/20* (2018.01); *G16H 70/20* (2018.01); *H04L 67/12* (2013.01); *H04L 67/535* (2022.05)

(58) Field of Classification Search
CPC ........ G16H 40/67; G16H 40/20; G16H 70/20; G16H 20/13; H04L 67/535; H04L 67/12; G06Q 20/127; G06Q 40/08
See application file for complete search history.

(56) References Cited

U.S. PATENT DOCUMENTS

| | | |
|---|---|---|
| 8,560,350 B2 | 10/2013 | Nadai |
| 9,697,335 B2 | 7/2017 | Joplin |

(Continued)

FOREIGN PATENT DOCUMENTS

WO WO 2010/124137 * 10/2010 ............. G06Q 50/00

OTHER PUBLICATIONS

AMA Telehealth policy, coding, and payment. AMA. Sep. 24, 2020. (Year: 2020).*

(Continued)

*Primary Examiner* — Christopher L Gilligan
*Assistant Examiner* — Tristan Isaac Evans
(74) *Attorney, Agent, or Firm* — The Small Patent Law Group

(57) ABSTRACT

A method for tracking duration of a remote telehealth encounter between a user computing device and a provider computing device via one or more computer networks is provided. The method includes receiving, at a telehealth control system, a signal from at least one of the user computing device or the provider computing device to initiate the remote telehealth encounter via the one or more networks, and tracking a duration of the remote telehealth encounter while both the user computing device and the provider computing device are connected to each other via the first encounter modality. The method also includes determining whether the remote telehealth encounter has ended, ending tracking of the duration of the remote telehealth encounter responsive to determining that the remote telehealth encounter has ended, and identifying a billing code based on the duration of the remote telehealth encounter.

17 Claims, 7 Drawing Sheets

(56) References Cited

U.S. PATENT DOCUMENTS

| | | | |
|---|---|---|---|
| 10,303,851 B2 | 5/2019 | Nguyen | |
| 10,949,602 B2 | 3/2021 | Snider | |
| 11,521,726 B2* | 12/2022 | Giles | G16H 30/40 |
| 11,587,688 B2* | 2/2023 | Joao | H04L 12/1818 |
| 11,990,247 B1* | 5/2024 | Lall | G16H 20/10 |
| 2002/0032582 A1* | 3/2002 | Feeney, Jr. | G07F 17/0092 |
| | | | 700/231 |
| 2002/0120466 A1 | 8/2002 | Finn | |
| 2004/0111293 A1 | 6/2004 | Firanek | |
| 2014/0257855 A1 | 9/2014 | Moore | |
| 2015/0294079 A1 | 10/2015 | Bergougnan | |
| 2017/0011179 A1 | 1/2017 | Arshad | |
| 2017/0011192 A1 | 1/2017 | Arshad | |
| 2017/0011193 A1 | 1/2017 | Arshad | |
| 2017/0011194 A1 | 1/2017 | Arshad | |
| 2017/0011196 A1 | 1/2017 | Arshad | |
| 2017/0011200 A1 | 1/2017 | Arshad | |
| 2018/0226158 A1* | 8/2018 | Fish | A61B 5/0022 |
| 2019/0034986 A1* | 1/2019 | Robinson | G06Q 30/0282 |
| 2020/0043579 A1 | 2/2020 | McEwing | |
| 2020/0327984 A1* | 10/2020 | Guinan | G06Q 30/04 |
| 2021/0065861 A1* | 3/2021 | Lamoncha | G16H 20/10 |
| 2021/0398668 A1* | 12/2021 | Chock | G06F 3/0482 |
| 2022/0384030 A1* | 12/2022 | Gong | G16H 20/10 |

OTHER PUBLICATIONS

Stack Overflow. Tracking "video duration watched" analytics from Java Script. 2015. (Year: 2015).*

Kiaghadi, Amin. Assessing COVID-19 risk, vulnerability and infection prevalence in communities. Plos One. Oct. 29, 2020. (Year: 2020).*

Gross. Coding Telemedicine Visits for Proper Reimbursement. Current Allergy and Asthma Reports (2020) 20:73. (Year: 2020).*

Khairat, Saif. Evaluating the Telehealth Experience of Patients with COVID-19 Symptoms Recommendations on Best Practices. Journal of Patient Experience 2020, vol. 7(5) 665-672. (Year: 2020).*

* cited by examiner

TELEHEALTH INTERACTION TRACKING SYSTEM AND METHOD

BACKGROUND

Many different types of services can be provided via distributed or long-distance systems. For example, telehealth systems can provide health-related services and information via electronic information and telecommunication technologies. These systems can allow for long-distance provider and customer interaction via video conferencing and/or telephone calls. With respect to telehealth systems, healthcare providers may be able to be reached for consultations, medical appointments, etc., for a variety of medical issues.

BRIEF DESCRIPTION

In one embodiment, a method for tracking duration of a remote telehealth encounter between a user computing device and a provider computing device via one or more computer networks is provided. The method includes receiving, at a telehealth control system, a signal from at least one of the first computing device or the provider computing device to initiate the remote telehealth encounter via the one or more networks, and determining whether both the user computing device and the provider computing device are connected to a first encounter modality to remotely interact with each other in the remote telehealth encounter via the one or more networks. The method also includes tracking a duration of the remote telehealth encounter while both the user computing device and the provider computing device are connected to each other via the first encounter modality, and determining whether one of the user computing device or the provider computing device leaves the remote telehealth encounter while another of the user computing device or the provider computing device remains in the remote telehealth encounter. The method includes pausing tracking of the duration of the remote telehealth encounter responsive to determining that one of the user computing device or the provider computing device leaves the remote telehealth encounter while another of the user computing device or the provider computing device remains in the remote telehealth encounter, and resuming tracking of the duration of the remote telehealth encounter responsive to both the user computing device and the provider computing device being connected to each other again via the first encounter modality or a second encounter modality. The method includes determining whether the remote telehealth encounter has ended, and ending tracking of the duration of the remote telehealth encounter responsive to determining that the remote telehealth encounter has ended, and identifying a billing code based on the duration of the remote telehealth encounter.

In one embodiment, another method for tracking duration of a remote telehealth encounter between a user computing device and a provider computing device via one or more computer networks is provided. The method includes receiving, at a telehealth control system, a signal from at least one of the user computing device or the provider computing device to initiate the remote telehealth encounter via the one or more networks, and tracking a duration of the remote telehealth encounter while both the user computing device and the provider computing device are connected to each other via the first encounter modality. The method also includes determining whether the remote telehealth encounter has ended, ending tracking of the duration of the remote telehealth encounter responsive to determining that the remote telehealth encounter has ended, and identifying a billing code based on the duration of the remote telehealth encounter.

In one embodiment, a tangible and non-transitory computer readable medium is provided. The storage medium includes instructions that direct one or more processors to receive a signal from at least one of the user computing device or the provider computing device to initiate the remote telehealth encounter via the one or more networks, determine whether both the user computing device and the provider computing device are connected to a first encounter modality to remotely interact with each other in the remote telehealth encounter via the one or more networks, track a duration of the remote telehealth encounter while both the user computing device and the provider computing device are connected to each other via the first encounter modality, determine whether one of the user computing device or the provider computing device leaves the remote telehealth encounter while another of the user computing device or the provider computing device remains in the remote telehealth encounter, pause tracking of the duration of the remote telehealth encounter responsive to determining that one of the user computing device or the provider computing device leaves the remote telehealth encounter while another of the user computing device or the provider computing device remains in the remote telehealth encounter, resume tracking of the duration of the remote telehealth encounter responsive to both the user computing device and the provider computing device being connected to each other again via the first encounter modality or a second encounter modality, determine whether the remote telehealth encounter has ended, end tracking of the duration of the remote telehealth encounter responsive to determining that the remote telehealth encounter has ended, and identify a billing code based on the duration of the remote telehealth encounter.

BRIEF DESCRIPTION OF THE DRAWINGS

In the drawings, reference numbers may be reused to identify similar and/or identical elements.

DETAILED DESCRIPTION

Figure 1:
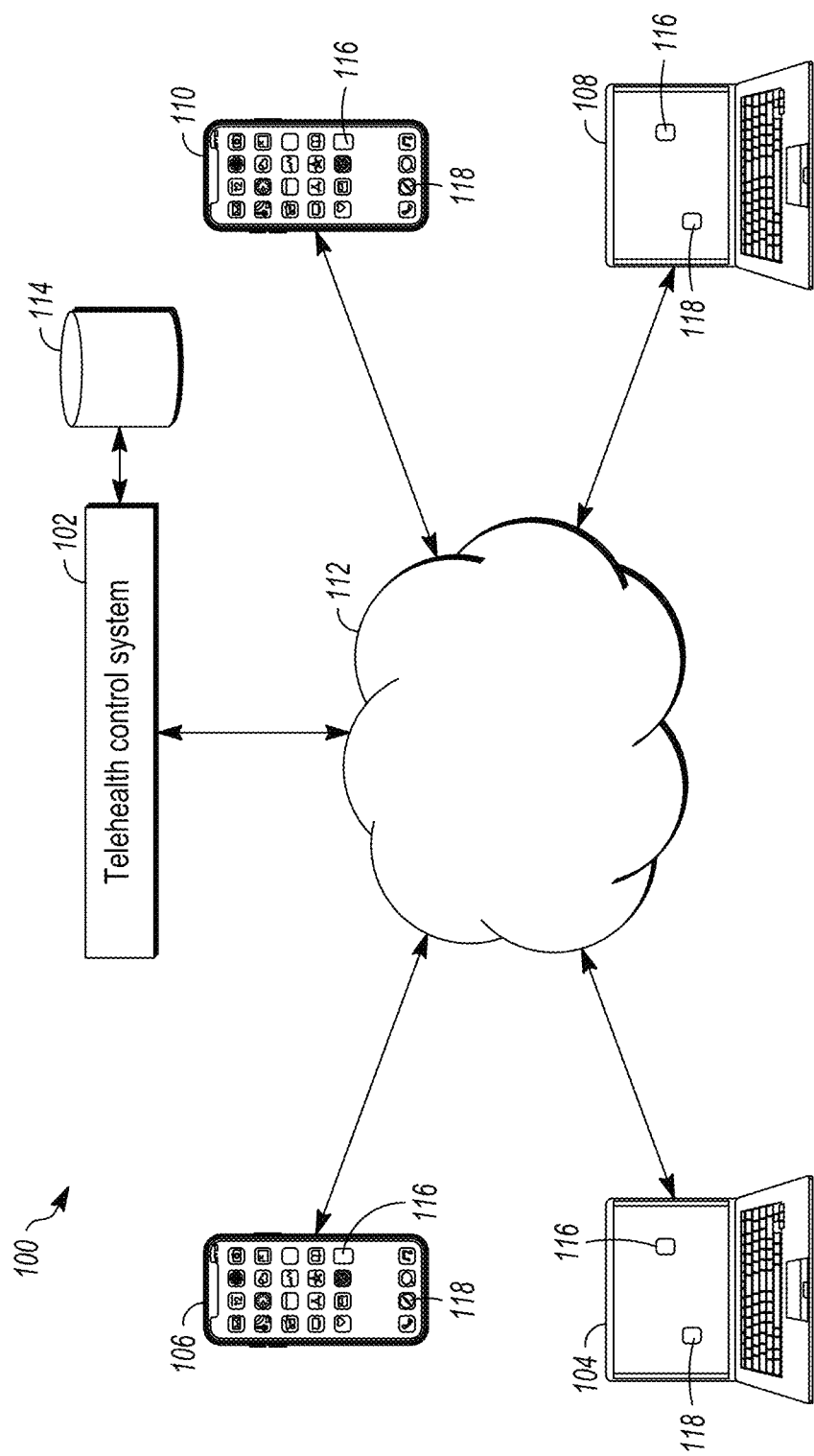
FIG. 1 illustrates one example of a telehealth system.

With respect to telehealth systems, patients may seek an appointment with a healthcare provider via a remote encounter (e.g., a videoconference or teleconference). The patients may be placed into a virtual waiting room until a suitable and available healthcare provider is found. Once the suitable and available healthcare provider is found, the remote encounter may be established, and the patients may remotely interact with the providers to receive medical care, advice, and the like.

Due to technological issues, the remote encounter may not begin or end at the same times, and/or interruptions may occur after the remote encounter has begun (but before conclusion of the remote encounter, such as where the provider and patient both sign-off of the interaction). For example, a provider may join a videoconference channel after the patient (or vice-versa), the patient may leave the encounter earlier than expected, or the like. Some telehealth interactions may be billed (and paid) according to how long the remote encounter lasts (with both provider and patient being able to communicate with each other). If the provider or patient joins the encounter before the other, the provider or patient leaves the encounter before conclusion of the encounter, and/or interruptions occur during the encounter, the duration of the encounter may be difficult to track and/or inaccurate for billing purposes. Additionally, some providers may report inaccurate durations of remote encounters for billing purposes. As a result, the present disclosure may address the need for an improved manner of tracking how long telehealth encounters last for billing (and other) purposes.

Some telehealth systems attempt to associate invoicing or billing codes with remote telehealth encounters (e.g., appointments conducted via videoconference and/or teleconference, rather than face-to-face interactions between the provider and patient in the same room). These codes can be used to charge insurance companies and/or patients for the services rendered by the providers, as well as to compensate the providers for the services provided to the patients. By way of example, these codes can include the Current Procedural Terminology (CPT) code set, the International Classification of Diseases (ICD) codes, Evaluation and Management (E&M) codes, Medical Dictionary for Regulatory Activities (MedDRA) codes, SNOMED codes, Logical Observation Identifiers Names and Codes (LOINC) codes, RxNorm codes, National Drug Code (NDC) codes, RadLex codes, and the like.

But due to various issues, the encounter may not begin or end at the same times, interruptions may occur after the remote encounter has begun, and/or providers may (intentionally or inadvertently) manually submit incorrect durations of encounters to the telehealth systems. For example, some mental health professionals or providers may conduct appointments with patients via videoconference and/or teleconference. The database storing the time spent between the patient and the provider over respective electronic devices. The patients and/or the insurance companies providing insurance benefits to the patients may be invoiced by the telehealth systems based on how long the patients and providers are engaged with each other via the telehealth appointment. Longer telehealth encounters may be billed using a different code than shorter telehealth encounters, and may be billed at higher fees or costs than shorter telehealth encounters. In an example embodiment, the length of time spent between a patient and a provider may be used to predict a diagnosis or provide a suggested diagnosis to the provider.

At least one embodiment of the tracking systems and methods described herein can monitor how long a provider and a patient are both concurrently involved or participating in a telehealth encounter so that the total duration of the encounter is determined. This total duration can be used to determine a proper billing or invoicing code to ensure that the correct amount is invoiced to the patient and/or insurance company, and the provider is compensated the correct amount. The systems and methods described herein can prevent patients and/or insurance companies from being overcharged, can prevent providers from being under compensated, and/or can reduce or eliminate some forms of fraud (where the providers report longer appointments than actually occurred). In one embodiment, a technical effect of the subject matter described herein can involve creation of a database or other memory structure based on the encounter durations that are tracked, where this database or other memory structure is used to determine and disburse payments to providers and/or to submit invoices or claims to a benefit system (e.g., an insurance company, a pharmacy benefit manager, etc.).

In one example, a technical effect can involve automatically dispensing a medication based on and/or responsive to identifying a billing code based on the duration of a telehealth encounter that is determined by the systems and/or methods described herein. Some medications may only be administered to patients after a provider has discussed the medications and/or other mediation options, as well as medical and/or mental issues of the patient. These discussions may rule out the usage of certain medications, reveal that certain medications may work better than others in assisting the patient, or the like. For example, some medications may not be prescribed and administered after only a brief discussion between a provider and a patient, but may require significant discussion between the provider and patient. The duration of the encounter between the provider and patient can be tracked to help ensure that a sufficient amount of time (e.g., at least a threshold amount of time, such as twenty minutes) has been spent during the discussion between the provider and patient before certain medications are prescribed and subsequently administered or provided.

FIG. 1 illustrates one example of a telehealth system 100. The telehealth system 100 may be used to establish and conduct remote encounters between healthcare providers and patients. A remote encounter may include an interaction or session (e.g., meeting, medical appointment, medical consultation, etc.) between a healthcare provider and a patient via video conference or teleconference while the healthcare provider and the patient are in different locations (e.g., different rooms, different buildings, different towns or cities, different zip codes, different states, or different countries). The healthcare provider can be a Doctor of Medicine, Doctor of Osteopathy, a podiatrist, a dentist, a chiropractor, a clinical psychologist, an optometrist, a nurse practitioner, a nurse-midwife, or a clinical social worker. While the examples described herein relate to the telehealth system 100 being used to establish remote encounters between healthcare providers and patients, not all embodiments of the inventive subject matter are limited to telehealth systems. For example, the telehealth system 100 optionally can be used to establish and conduct remote encounters between real estate agents and clients, between attorneys and clients, courts and parties to a legal proceeding, teachers and students, governmental meetings, voter and election systems, or any other service provider and customer who are connected via an electronic communication system.

The telehealth system 100 includes a control system 102 that represents hardware circuitry having and/or connected with one or more processors (e.g., microprocessors, field programmable gate arrays, integrated circuits, etc.) that perform the operations described in connect with the control system 102. The control system 102 communicates (wirelessly and/or via wired connections) with provider computing devices 104, 106 and user or patient computing devices 108, 110. The computing devices 104, 108 can represent laptop computers, desktop computers, tablet computers, or the like, and the computing devices 106, 110 can represent mobile phones. While only two patient computing devices and only two provider computing devices are shown, the telehealth system 100 can establish communication between many more patient computing devices and many more provider computing devices.

The control system 102 can manage a virtual encounter between the providers and patients by establishing a communication channel between a computing device 104 or 106 of the provider(s) and a computing device 108 or 110 of the patient. This communication channel can be a videoconference or a teleconference that extends through one or more computer networks 112, such as the Internet, one or more intranets, one or more local area networks, or the like. The computing devices 104, 106, 108, 110 may have software applications 116 installed or otherwise running thereon to establish a secure connection between (a) the provider computing device 104 or 106 and (b) the patient computing device 108 or 110. These software applications 116 can be commercial or proprietary applications 116 used by a company or government to manage the remote encounters between providers and patients. The applications 116 can be installed in internal computer memories of the computing devices 104, 106, 108, 110 or may be accessed via web pages 118. One example of such a software application 116 or service is MDLIVE healthcare services that provides remote healthcare services e.g., via telephone, video, email, mobile devices, or a global computer network. The secure connection can extend through the network(s) 112 to ensure confidentiality of the information communicated between the provider and the patient. For example, the videoconference or teleconference channel can extend through one or more digital subscriber lines, cable modems, network fibers, wireless networks, satellite networks, broadband over powerline connections, etc., using the transmission control protocol over Internet protocol, or another protocol.

A patient can submit a request for a virtual encounter to the control system 102 using the software application 116 installed on or accessible on a website 118 via a patient computing device 108 or 110. In FIG. 1, reference number 118 can represent this web site that is accessed by an Internet browser. This request can identify the patient, one or more health consultation needs of the patient, and other information. The health consultation needs may identify health issues or questions that the patient wishes to have resolved, answered, or otherwise addressed by a remote encounter with a provider. The control system 102 can use this information to identify one or more appropriate providers. For example, if the request identifies an issue related to the skin of the patient, then the control system 102 can determine that the appropriate provider is a dermatologist. If the request identifies an issue related to diabetes mellitus, then the control system 102 can determine that the appropriate provider is an endocrinologist. If the request identifies a mental health issue, then the control system 102 can determine that the appropriate provider is a psychologist, and so on. The control system 102 may only send notifications to providers for the virtual encounters where the providers have education, expertise, training, and/or certification to provide service to treat the identified issue.

The control system 102 can include or have access to a tangible and non-transitory computer readable medium, such as a database within a computer memory 114, that stores different specialties of the providers, contact information (e.g., phone numbers) of the providers, and so on. The control system 102 can refer to information stored in the memory 114 to determine appropriate providers with which the videoconference or teleconference with the patient can be provided (based on information included in the request submitted by the patient).

The control system 102 can determine a beginning or commencement time at which a remote telehealth encounter begins. This time can be identified by the control system 102 determining a time at which the provider computing device 104 or 106 is connected to a videoconference or teleconference channel and a time at which the patient computing device 108 or 110 is also connected to the same videoconference or teleconference channel. For example, the control system 102 can identify the beginning time as the time at which the latter of (a) the time that the provider joins the videoconference or teleconference and (b) the time that the patient joins the videoconference or teleconference. The control system 102 may not identify the beginning time as occurring if one of the patient or provider has not joined the videoconference or teleconference. For example, if the provider computing device 104, 106 joins the videoconference or teleconference at 10:09 am and then leaves the videoconference or teleconference (e.g., due to a technical issue or failure) at 10:10 am, the patient computing device 108, 110 joins the videoconference or teleconference at 10:11 am, and the provider computing device 104, 106 re-joins the videoconference or teleconference at 10:12 am, then the control system 102 can identify the beginning or commencement time as 10:12 am.

The control system 102 can include a clock or other device that can be used to track the duration of the telehealth encounter. This duration may be measured as the total time that both the provider computing device 104 or 106 and the patient computing device 108 or 110 are connected to the videoconference or teleconference channel. The duration being tracked or timed may be paused if either or both the provider computing device 104 or 106 and the patient computing device 108 or 110 disconnects or drops from the videoconference or teleconference. For example, both the provider computing device 104 or 106 and the patient computing device 108 or 110 may be connected to the videoconference or teleconference channel at 10:12 am but the patient computing device 108 or 110 loses its connection to the network 112 (and, therefore, disconnects from videoconference or teleconference channel) at 10:35 am. The control system 102 can determine that the beginning time is 10:12 am and the duration is tracked form 10:12 am to 10:35 am. The duration is then paused by the control system 102. That is, the control system 102 determines that the encounter has lasted 13 minutes but does not continue to add to or lengthen the duration of the telehealth encounter.

The control system 102 can monitor the videoconference or teleconference channel to determine when both the provider computing device 104 or 106 and the patient computing device 108 or 110 are subsequently connected to the videoconference or teleconference. For example, once the patient computing device 108 or 110 that was dropped from the videoconference or teleconference (e.g., due to a loss of connection to the network 112) re-connects to the videoconference or teleconference, the control system 102 can return to tracking the duration of the telehealth encounter. The control system 102 can repeat this pausing and restarting of the duration of the telehealth encounter if the provider computing device 104 or 106, or the patient computing device 108 or 110, disconnects and then reconnects with the videoconference or teleconference. The control system 102 may not pause or restart counting or tracking the duration of the encounter so long as both the provider computing device 104 or 106 and the patient computing device 108 or 110 remain connected with the videoconference or teleconference.

The control system 102 can terminate or otherwise end tracking the duration of the telehealth encounter responsive to one or more termination events occurring. One example of a termination event is both the provider computing device 104 or 106 and the patient computing device 108 or 110 disconnecting or otherwise leaving the teleconference or videoconference. Another example of a termination event is the control system 102 receiving a signal from the provider computing device 104, 106 or the patient computing device 108, 110. This signal can indicate that the telehealth encounter has ended. For example the provider or patient can press one or more icons, buttons, or the like, on the respective provider computing device 104, 106 or patient computing device 108, 110 to indicate that the encounter is completed. Optionally, the control system 102 may only identify the termination of the encounter when the signal is received from the patient computing device 108 or 110, but not when the signal is received from the provider computing device 104, 106. This can help reduce instances or the likelihood of a fraudulent situation where a provider could otherwise allow the control system 102 to continue tracking the duration of the encounter after the patient has left the videoconference or teleconference. Or, the control system 102 may only identify the termination of the encounter when the signal is received from both the patient computing device 108 or 110, and from the provider computing device 104, or 106.

The control system 102 can continue to track the duration of the encounter even when the patient and/or provider changes a modality of the encounter. Different modalities of the encounter can be different modes or types of interactions, such as a videoconference, a teleconference (e.g., a phone call between the provider and patient), or a videoconference where one participant (e.g., the provider or patient) does not have video, does not have a display device, does not have a camera, does not permit the computing device to display a video, etc. Other modalities can be a chat room, text or short message service (SMS) messages, etc. One or both of (a) the provider computing device 104 or 106 and/or (b) the patient computing device 108 or 110 can change modalities of the encounter during the encounter. For example, due to a reduced network bandwidth, a failure in a camera or other device, or the like, the provider computing device 104, 106 and/or the patient computing device 108, 110 may lose the ability to continue in the video conference and may need to switch to a teleconference or text messages to maintain communication with the other of the provider computing device 104, 106 or the patient computing device 108, 110. The control system 102 can pause the duration of the encounter while the modality of the encounter is being switched, and then return to tracking the duration of the encounter once the modality is changed and the patient and provider are communicating once again.

The control system 102 can determine the total duration of the encounter after the encounter is terminated. The control system 102 can then communicate this duration to a billing system of an insurance company or a pharmacy benefit manager device (shown as 628 in FIG. 3). Optionally, the control system 102 can determine a billing or invoice code based on the duration. Different durations may be associated with different CPT (or other) billing codes. The control system 102 can select the billing code using the duration of the encounter that was determined. This billing code can then be submitted to the insurance company or the pharmacy benefit manager device (e.g., for billing the insurance company and/or patient, and/or for selecting a medication to be dispensed).

For example, a client engages a pharmacy benefit manager (PBM) 628 (shown in FIG. 3) to offer a drug benefit program to patients. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. In conjunction with receiving the co-pay (if any) from the member and dispensing the prescribed drug to the member, a pharmacy submits a claim to the PBM for the prescribed drug. The PBM may perform certain adjudication operations including verifying the eligibility of the member, reviewing the formulary to determine appropriate co-pay, coinsurance, and deductible for the prescribed drug, and performing a drug utilization review (DUR) on the member. In some embodiments, the PBM may determine and/or classify the prescribed drug and associate the drug with an acute medication pharmacy provider network or a maintenance medication pharmacy provider network.

The PBM may then provide a response to the pharmacy following performance of the aforementioned operations. As part of the adjudication, the client (or the PBM on behalf of the client) may ultimately reimburse the pharmacy for filling the prescribed drug when the prescription drug claim was successfully adjudicated. The aforementioned adjudication operations generally occur before the co-pay is received and the prescribed drug dispensed. However, the operations may occur simultaneously, substantially simultaneously, or in a different order. In addition, more or less adjudication operations may be performed as part of the adjudication process.

In one example, the PBM may use the billing code and/or encounter duration output by the control system 102 to adjudicate a claim for a medication, which can involve automatically filling the corresponding prescription (e.g., without further operator intervention) or automatically sending instructions to direct a system or person to fill the corresponding prescription. The adjudication module can communicate the adjudication response to a packaging subsystem that can fill the corresponding prescription.

Figure 2:
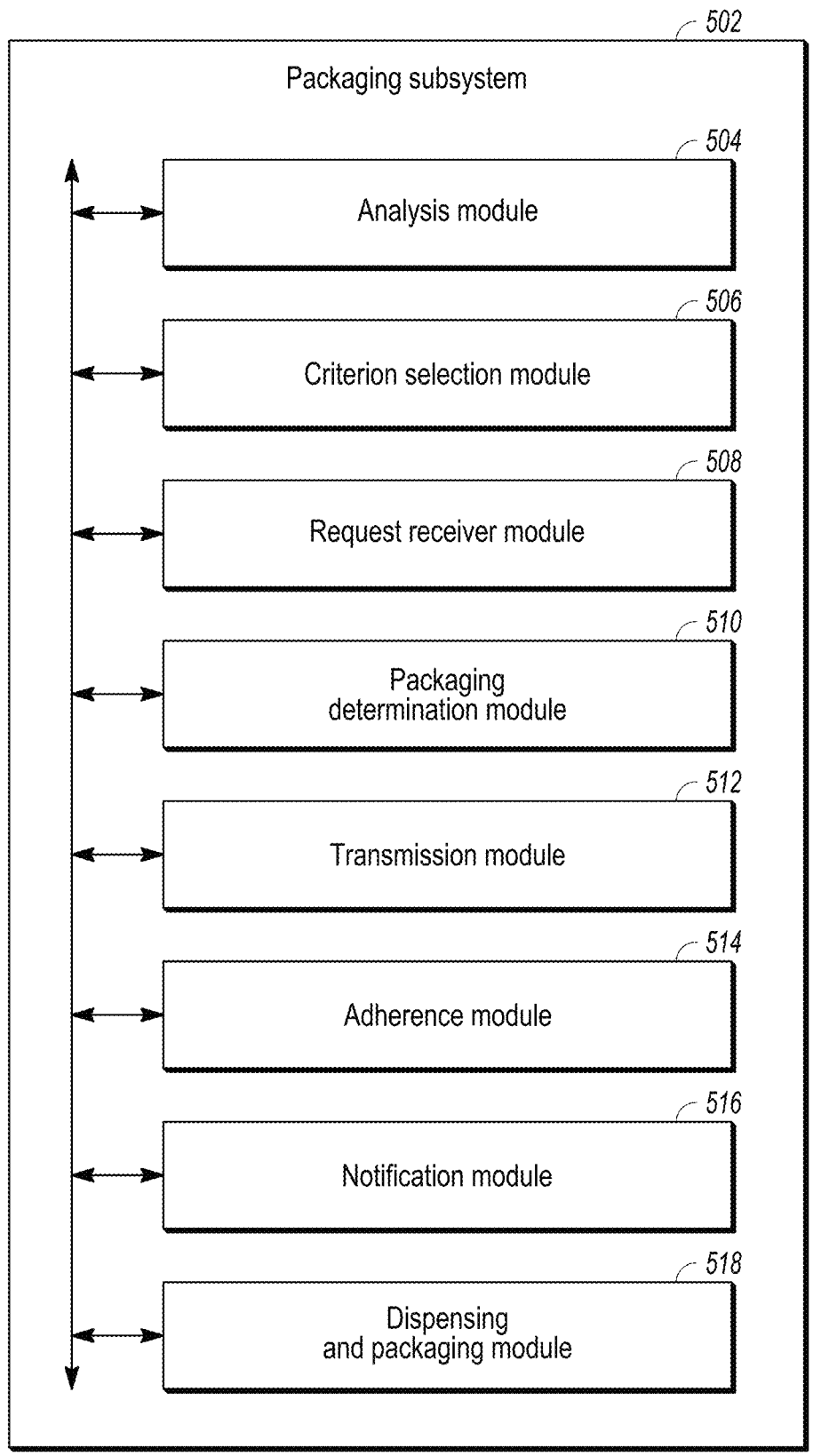
FIG. 2 illustrates an example packaging subsystem.

FIG. 2 illustrates an example packaging subsystem 502. One or more modules are communicatively coupled and included in the packaging subsystem 502 to package prescription drugs based on the adjudication response, billing code, and/or encounter duration. For example, the billing code and/or encounter duration may be associated with a prescription for a medication, but the packaging subsystem 502 may not dispense the prescribed medication without the billing code or encounter duration that is output by the control system 102. The modules of the packaging subsystem 502 that may be included are an analysis module 504, a criterion selection module 506, a request receiver module 508, a packaging determination module 510, a transmission module 512, an adherence module 514, a notification module 516, and a dispensing and packaging module 518. Other modules may also be included.

In some embodiments, the modules of the packaging subsystem 502 may be distributed so that some or all of the modules are deployed in the control system 102. In one embodiment, the modules are deployed in memory and executed by a processor or more than one processor coupled to the memory. The functionality contained within the modules 504, 506, 508, 510, 512, 514, 516, 518 may be combined into a lesser number of modules, further divided among a greater number of modules, or redistributed among existing modules. Other configurations including the functionality of the modules 504, 506, 508, 510, 512, 514, 516, 518 may be used.

In some embodiments, the analysis module 504 analyzes prescription drugs that have been prescribed to a patient population and/or taken by the patient population and identifies one, or more than one, prescription drugs among the prescribed and/or taken prescription drugs as being a maintenance drug that could be fulfilled through prescription bottle fulfillment or blister packaging fulfillment. The patient population may include all members of a single client, a subset of all members of a single client, al, or a subset of members of multiple clients, or the like. For example, certain types of drugs may be commonly taken by the population and are in the form of a pill or other type of drug that could be packaged in at least blister packaging. Data reflecting the prescription drugs prescribed to the patient population may come from data received from prescribers, from an electronic prescribing network (e.g., directly from the network or through a device associated with an entity responsible for electronic prescribing network), PBMs, or otherwise. Data reflecting the prescription drugs taken by the patient population may come from claims data, claims data received from another source, or otherwise.

The analysis module 504 may thereby identify one, or more than one, type of drugs for the patient population as being candidates for selection by the criterion selection module 506. For example, a prescription drug that is taken through an inhaler may be identified as not being a candidate for selection because of unavailability through prescription bottle fulfillment or blister packaging fulfillment (e.g., but rather as being available for unit-of-use fulfillment), while a prescription drug taken in tablet form may be identified as being a candidate for selection as being available through prescription bottle fulfillment or blister packaging fulfillment.

In some embodiments, the analysis module 504 uses drug data (as stored in the database 114 and/or in another database) in identifying candidate drugs for selection. For example, the drug data may include packaging information regarding the prescription drugs. In some embodiments, the pharmacy device 102 analyzes or accesses its drug inventory including, in some embodiments, packaging information to identify candidate drugs for selection.

The analysis of the prescription drugs to identify prescription drugs as being a maintenance drug may be made by the analysis module 504 in a number of different methods. In some embodiments, a prescription drug is identified as a maintenance medication or drug (or as commonly used as a maintenance medication or drug) in the drug data. Such identification may be made by the manufacturer of the prescription drug, a health care provider associated with the prescription drug, a PBM or other benefit manager associated with the prescription drug, a governmental organization, or a different entity.

In some embodiments, a PBM may analyze the claim data of one or a number of members to identify prescription drugs as maintenance medications. For example, claims that reflect continuing usage by members over a period of time (e.g., multiple refills) may be identified as maintenance drugs, while claims that reflect acute usage by members (e.g., one-time usage during a certain time period) may be identified as not being a maintenance medication.

The criterion selection module 506 selects blister packaging criterion used for some or all of the drugs (e.g., in one class, or more than one class of drugs) based on analysis performed by the analysis module 504. In general, the blister packaging criterion establishes one, or more than, criterion for determining whether a prescription drug should be filled with blister packaging instead of other packaging that may be available (e.g., a prescription bottle of a particular size). The blister packaging criterion may be made in general for a type of prescription drug across an entire patient population, or may be specific to certain patients or groups of patients.

In some embodiments, blister packaging includes a cavity or pocket made from a formable web, usually a thermoformed plastic. In some embodiments, blister packaging includes a backing of paperboard or a lidding seal of aluminum foil or plastic. Non-blister packaging generally includes other types of prescription drug containers such as bottles in a variety of sizes that are sealed with lids.

In some embodiments, the analysis module 504 reviews a number of commonly used maintenance drugs by the patient population. The number may be a threshold, may be a number designated by a person or entity associated with the creation, deployment, and/or usage of the packaging determination subsystem 502. By way of example, the number and type of drugs may be such as to enable a certain percentage usage across the patient population of blister packaging on at least one prescription drug that is likely to be taken by a member in the patient population. In some embodiments, not all prescription drugs taken by a patient or member are ultimately selected for blister packaging. Rather, a subset of prescription drugs are selected while member adherence improves for all prescription drugs (including those not in blister packaging).

In some embodiments, the analysis module 504 utilizes one, or more than one, models and/or classifiers for use in analysis and/or identification of prescription drugs as being a common maintenance drug. The analysis module 504 may include models and/or classifiers such as group method of data handling, naive bayes, k-nearest neighbor algorithm, majority classifier, support vector machine, logistic regression, uplift modeling, or the like. Such functionality may enable a more sophisticated selection of prescription drugs to be packaged in blister packaging, and/or may further individualize the selection of one, or more than one, prescription drug to be packaged in blister packaging for a particular patient.

The analysis module 504 determines that a person (e.g., a member of a pharmacy benefit plan and/or a patient of a pharmacy) has had prescription drugs that have previously been filled. The drugs may have been filled through an entity making the determination through the analysis module 504, or through another entity (e.g., by a retail pharmacy or a mail order pharmacy). The determination relative to the member may be made through analysis of the claims data associated with the member or otherwise.

In some embodiments, the adherence module 514 may determine the adherence of the member. When the member's adherence is below a certain threshold, the analysis performed by the analysis module 504 may be made to determine whether the member is an appropriate candidate to receive (or continue to receive) blister packaging for one, or more than one, type of prescription drug. When the member's adherence is above a certain threshold, the member may not be a candidate to receive blister packaging (e.g., for adherence reasons) based on the analysis performed by the analysis module 504.

The request receiver module 508 receives a request for a prescription drug prescribed to the member. In some embodiments, the request is an adjudication request associated with a fulfillment request to fill the prescription drug. In general, the adjudication request reflects that the member is seeking to have a prescription drug filled as either a new prescription or renewal. In some embodiments, the request is a fulfillment request to fill the prescription drug on behalf of the patient.

The packaging determination module 510 determines packaging to use to fill the prescription drug associated with the received request. In some embodiments, the determination of the packaging may be in response to receipt of the request for the prescription drug.

In some embodiments, the packaging determination made by the packaging determination module 510 is based on whether a blister packaging criterion has been met. The blister packaging criterion may identify a single prescription drug or multiple prescription drugs for blister packaging and reflect that a member or patient has had a prescription drug of the same or similar type that has previously been filled. For example, this determination may be on the basis of the patient (e.g., low patient adherence), on the basis of the prescription drug (e.g., commonly available and in a form that can be filled in blister packaging or is available in blister packaging), and the like. By making the determination, the packaging determination module 408 may identify the prescription drug associated with the current request to be filled with blister packaging.

By way of example, the prescription drug may be selected by the packaging determination module 408 among the prescription drugs that have previously been filled on behalf of the member to fill in blister packaging on behalf of the member. A determination may then be made by the packaging determination module 510 that the blister packaging criterion has been met based on selection of the prescription drug to fill in the blister packaging and receipt of the request for the prescription drug.

In some embodiments, the transmission module 512 transmits a blister fill instruction based on receipt of the request and a determination that the blister packaging criterion has been met and/or based on receipt of the adjudication response from the transition module 410. The blister fill instruction may reflect that the pharmacy device 102 is to fill the prescription drug utilizing blister packaging. In some embodiments, an adjudication response includes a blister fill instruction. In other embodiments, the blister fill instruction is sent separate from the adjudication response.

As described above, adherence may be determined by the adherence module 514 to determine whether a member should receive blister packaging. In some embodiments, however, the adherence module 514 may determine adherence before and after a prescription drug is provided in blister packaging to determine a difference in adherence for the prescription drug provided in blister packaging and other prescription drugs that have not been provided to the member in blister packaging. Thus, the adherence module 514 may operate in conjunction with the analysis module 504 and/or the criterion selection module 506 to determine whether the member should receive the prescription drug in blister packaging as opposed to a fill in a prescription bottle.

By way of example, the adherence module 514 measures prior prescription drug adherence of the member prior to transmission of an adjudication response and measures after prescription drug adherence of the member for a period of time after transmission of the blister fill instruction, the period of time including at least one time period during which the prescription drug was prescribed to be taken by the member prior to prescription drug refill, and compares the prior prescription drug adherence and the after prescription drug adherence. The notification module 516 generates a notification based on comparison of the prior prescription drug adherence and the after prescription drug adherence. In some embodiments, the notification reflects that the after prescription drug adherence of the member is greater than the prior prescription drug adherence for both the prescription drug in blister packaging and any other drugs prescribed to be taken by the member that are not in blister packaging. As a result of the difference in adherence, the benefit manager, or another party, may receive a greater amount of reimbursement directly or indirectly from the client.

Not every prescription drug prescribed to the patient may be packaged in blister packaging. In some embodiments, the request receiver module 508 receives an additional request for an additional prescription drug prescribed for the member and the packaging determination module 510 determines that the blister packaging criterion has not been met based on a drug type of the prescription drug. As such, the packager of the prescription drugs (or the client, benefit manager, etc.) may not incur increased packaging cost for every prescription drug, but merely a subset of one or more than one prescription drug fulfilled for the member. The transmission module 512 may therefore transmits an additional response to the additional request. In some embodiments, the additional request reflects that the pharmacy is to fill the prescription drug accordance to standard fulfillment instructions.

The dispensing and packaging module 518 dispenses and packs a prescription drug into packaging (e.g., the prescription container). In some embodiments, the dispensing and packaging module 518 dispenses and packs the prescription drug into blister packaging based on receipt of the request for the prescription drug, receipt of the adjudication response, and a determination that the blister packaging criterion has been met. In some embodiments, the dispensing and packaging module 518 dispenses and packs the prescription drug into based on receipt of the blister fill instruction. The blister packaging may be performed by the pharmacy device 102 (e.g., at or before the time of fill), by a drug manufacture of the prescription drug, or otherwise. Once packed, the prescription drug may be provided to the member through mail order, in person (e.g., at a retail pharmacy), or otherwise.

Figure 3:
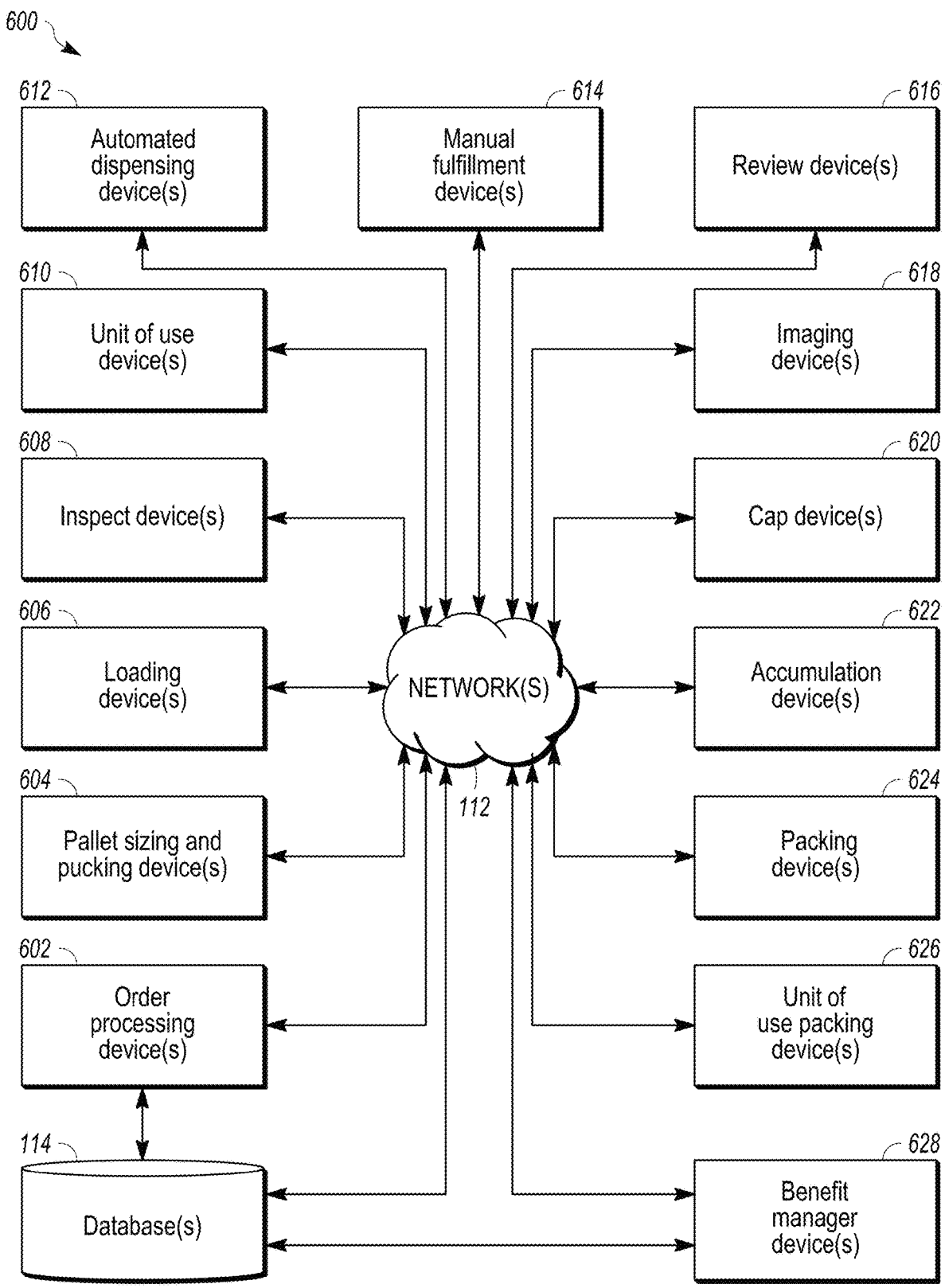
FIG. 3 is a block diagram of an example filling system.

FIG. 3 is a block diagram of an example filling system 600, according to an example embodiment. While the system 600 is generally described as being deployed in a high volume pharmacy (e.g., a mail order pharmacy, a direct delivery pharmacy, and the like), the system 600 may otherwise be deployed. Some embodiments of a high volume pharmacy are described in U.S. Pat. No. 9,697,335; application Ser. No. 14/807,596; titled "Methods and systems for automated pharmaceutical dispensing," which is hereby incorporated by reference. In some embodiments, the system 600 includes the system 100 and/or the subsystem 502. The control system 102 of FIG. 1 may be reflected as devices 602-626 in the system 600.

The system 600 may include an order processing device 602 that receives information about prescriptions being filled at a pharmacy in which the order processing device 602 is deployed. For example, the order processing device 602 may receive the billing code output by the control system 102, along with a prescription for a medication that was provided during or subsequent to the telehealth encounter. The order processing device 602 may track a prescription order as the order is fulfilled. A prescription order may include one or more than one prescription to be filled by the pharmacy. The order processing device 602 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 602 may operate in combination with the benefit manager device 108. In some embodiments, the order processing device 602 includes the packaging subsystem 502 and one or more than one of the modules of the packaging subsystem 502.

The order processing device 602 and/or the benefit manager device 108 may be in communication directly (e.g., through local storage) and/or through the network 112 (e.g., in a cloud configuration or software as a service) with the database 114 (e.g., as may be retained in memory or otherwise). The database 114 may store order data, member data, claims data, drug data, prescription data, and/or plan sponsor data. Other data may be stored in the database 114.

The order data may include data related to the order of prescriptions including the type (e.g., drug name and strength) and quantity of each prescription in a prescription order. The order data may also include data used for completion of the prescription, such as prescription materials. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The prescription data may include information regarding prescriptions that may be issued by prescribers on behalf of patients, who may be members of the drug benefit plan, for example to be filled by a pharmacy. Examples of the prescription data include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

The system 600 may include a pallet sizing and pucking device 604, a loading device 606, an inspect device 608, a unit of use device 610, an automated dispensing device 612, a manual fulfillment device 614, a review device 616, an imaging device 618, a cap device 620, an accumulation device 622, a packing device 624, and/or a unit of use packing device 626. The system 600 may also include additional devices. The order processing device 602 may direct at least some of the operations of these devices 604-626. In some embodiments, operations performed by one of these devices 604-626 may be performed sequentially, or in parallel with the operations of another device as may be coordinated by the order processing device 602. The order processing device 602 may receive the adjudication response described above and control (e.g., direct through generation and communication of signals to) the devices 604-626.

In some embodiments, the system 600 may transport prescription drug containers by use of pallets. The pallet sizing and pucking device 604 may configure (e.g., arrange or otherwise move) pucks in a pallet. A pallet may be a transport structure for a number of prescription containers, and may include a number of cavities. A puck may be placed in one or more than one of the cavities in a pallet by the pallet sizing and pucking device 604. A puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 602 based on prescriptions which the order processing device 602 decides to launch based on the adjudication response. For example, responsive to receiving the adjudication response, the order processing device 602 can decide to launch one or more pallets containing the medication(s) identified in or otherwise associated with the adjudication response. In general, prescription orders in the database 114 reside in one or more than one queues, and are generally launched in a first-in-first-out order. The order processing device 602, however, may use logic and a variety of factors (e.g., the adjudication response) to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, receipt of the adjudication response, whether valid paperwork for the order has been received, and/or similar orders for the same pharmaceutical that are already to be launched. The logic may be implanted directly in the pallet sizing and pucking device 604, in the order processing device 602, in both devices 602, 604, or otherwise. Once a prescription is set to be launched, a puck suitable for the appropriate size of container for that prescription may be positioned in a pallet by a robotic arm or pickers. The pallet sizing and pucking device 604 may launch a pallet once pucks have been configured in the pallet.

The loading device 606 may load prescription containers into the pucks on a pallet by a robotic arm, pick and place mechanism, or the like. In one embodiment, the loading device 606 has robotic arms or pickers to grasp a prescription container and move it to and from a pallet. The loading device 606 may also print a label which is appropriate for a container that is to be loaded onto the pallet, and apply the label to the container. The pallet may be located on a conveyor assembly during these operations.

The inspect device 608 may verify that containers in a pallet are correctly labeled and in the correct spot on the pallet. The inspect device 608 may scan the label on one or more than one container on the pallet. Labels of containers may be scanned or imaged in full or in part. Such imaging may occur after the container has been lifted out of its puck by a robotic arm, picker, or the like, or may be otherwise scanned or imaged while retained in the puck.

The unit of use device 610 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like.

The automated dispensing device 612 may include one or more than one devices that dispense prescription drugs or pharmaceuticals into prescription containers such as prescription bottles and blister packs in accordance with one or multiple prescription orders. The automated dispensing device 612 dispenses a number of prescription drugs or pharmaceuticals according to the output from various methodology as described herein. Such methodology can include whether a pharmacy associated with the claims adjudication data is included within the pharmacy provider network type that is associated with the prescribed drug; adjudicating a pharmacy claim for the prescribed drug through the pharmacy, the claims adjudication data, and determination of whether the pharmacy is included within the pharmacy provider network type; communicating an adjudication response indicative of the pharmacy claim that is adjudicated to an order processing device at a pharmacy filling system via a communication network; or combinations thereof. In general, the automated dispensing device 612 may include mechanical and electronic components with, in some embodiments, software and/or logic to facilitate pharmaceutical dispensing that would otherwise be performed in a manual fashion by a pharmacist and/or pharmacist technician. For example, the automated dispensing device 612 may include blister pack machines that dispense and pack drugs into a blister pack and/or a pill dispensing machines that that dispense and pack drugs into a prescription bottle.

The manual fulfillment device 614 may provide for manual fulfillment of prescriptions. For example, the manual fulfillment device 614 may receive or obtain a container and enable fulfillment of the container by a pharmacist or pharmacy technician. In some embodiments, the manual fulfillment device 614 provides the filled container to another device in the system 600 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter).

The review device 616 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 616 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 618 may image containers once they have been filled with pharmaceuticals. The imaging device 618 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon.

The cap device 620 may be used to cap certain types of prescription containers such as a prescription bottle. In some embodiments, the cap device 620 may provide a type of cap in accordance with a patient preference (e.g., a preference regarding child resistance), a plan sponsor preference, a prescriber preference, or the like. The cap device 620 may also etch a message into the cap, although this process may be performed by a subsequent device.

The accumulation device 622 accumulates various containers of prescription drugs in a prescription order. The accumulation device 622 may accumulate prescription containers from various areas of the pharmacy. For example, the accumulation device 622 may accumulate prescription containers from the unit of use device 610, the automated dispensing device 612, the manual fulfillment device 614, and the review device 616.

The packing device 624 packages a prescription order in preparation for shipping the order. The packed prescription order may package prescription containers that are of the same dimensions or different (e.g., different prescription bottle sizes, blister packaging and prescription bottle, and the like). The packing device 624 may box or bag the fulfilled prescription order for delivery. The packing device 624 may further place inserts into the box or bag. For example, bulk prescription orders may be shipped in a box, while other prescription orders may be shipped in a bag which may be a wrap seal bag. The packing device 624 may label the box or bag with the address and a recipient's name. The packing device 624 may sort the box or bag for mailing in an efficient manner (e.g., sort by delivery address). The packing device 624 may include ice or temperature sensitive processing for prescriptions which are to be kept within a temperature range during shipping in order to retain efficacy or otherwise. The ultimate package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise. The unit of use packing device 626 packages a unit of use prescription order in preparation for shipping the order. The unit of use packing device 626 may include manual scanning of containers to be bagged for shipping to verify each container in the order.

A fulfillment gateway system can be provided or used to control and/or coordinate operations of the control system 102, the packaging subsystem 502, and/or the filling system 600. For example, the gateway system can receive prescription orders, adjudication responses associated with the prescription orders, or the like, and associate the prescription orders with order messages containing information for the packaging subsystem 502 and/or the filling system 600.

Figure 4:
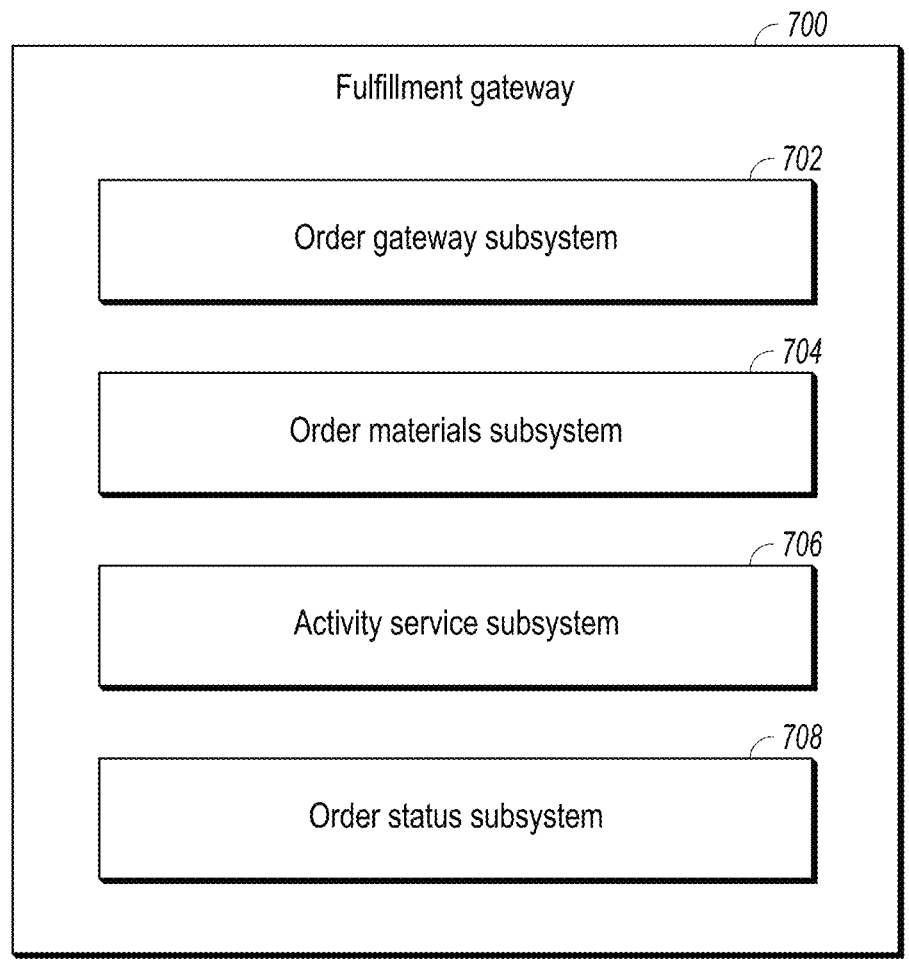
FIG. 4 illustrates one example of a fulfillment gateway system.

FIG. 4 illustrates one example of a fulfillment gateway system 700. The fulfillment gateway system 700 may include an order gateway subsystem 702, an order materials subsystem 704, an activity service subsystem 706, and/or an order status subsystem 708. Other subsystems may also be included. The order gateway subsystem 702 manages communications for the fulfillment gateway system, including coordination of communications to/from the order materials subsystem 704, the activity service subsystem 706, and an order status subsystem 708. The order gateway subsystem 702 also can receive prescription orders and/or the billing codes described herein, and fulfill the prescriptions as described herein. For example, the order gateway subsystem 702 provides communications for receiving prescription orders from the order processing station and/or the billing codes from the control system 102. The order gateway subsystem 702 also may provide a storage unit for order messages that are assigned or not yet assigned to various fulfillment devices 612, 614.

The order materials subsystem 704 obtains order materials and/or adjudication responses for use at the fulfillment devices 612, 614. The order materials are an electronic record of information needed by the fulfillment devices 612, 614 to implement fulfillment of the prescription according to policies and preferences of patients, clients, and the fulfillment devices 612, 614. Thus, an electronic record can be developed for the fulfillment devices 612, 614, thereby limiting reliance of the fulfillment devices 612, 614 on other devices for information. In some embodiments, order materials and/or adjudication response are stored at the fulfillment devices 612, 614. In other embodiments, order materials and/or adjudication responses are aggregated from the order data by accessing the database 114. The order materials and/or adjudication responses can be included in the order message associated with the prescription order. Order materials and/or adjudication responses may include at least some portions of the patient data, the client data, the pharmacy data, prescription parameters, dispensation preferences and/or prescription materials.

Prescription materials are a type of order materials that include information regarding the prescription drug for inclusion with the fulfilled prescription. The prescription materials may include electronic information regarding drug interaction warnings, recommended usage, possible side effects, etc. for printing and inclusion with the fulfilled prescription for shipping. The order materials subsystem 704 may electronically format the order materials into useable fields. For example, the patient data and/or or the client data may include dispensation preferences such as the inclusion of an invoice with the fulfilled prescription, the inclusion of a return envelope for remitting payment with the fulfilled prescription, the use of a child proof cap, the inclusion of reminders printed on a label, cap or leaflet, the inclusion of consumer survey leaflets, the inclusion of a message encouraging therapy adherence on a label, cap or leaflet, or the like.

The activity service subsystem 706 tracks operations performed by the fulfillment gateway 700 and stores the operations for historical reporting and visibility as activity data. In some embodiments, through the order gateway subsystem 702, the order status subsystem 708 receives order status updates and/or adjudication responses periodically or on a non-periodic basis. The order status subsystem 708 keeps an update on a prescription order as the order progresses through the fulfillment gateway 700 for possible intervention in the fulfillment. The order status subsystem 708 has the capability of instructing that a prescription order be cancelled, paused, or changed based on the adjudication response. Cancelling, pausing, or changing the prescription order may avoid the fulfillment of prescriptions that are no longer needed by the patient or that are denied as a result of the adjudication response, and are therefore of little use. For example, if a patient decides to transfer the prescription to another pharmacy or the adjudication response indicates that the prescription fill request is denied, the order status subsystem 708 can determine the status of the order and send a command to cancel the prescription order via the order gateway subsystem 702 to the fulfillment devices 612, 614. An example of changing the prescription order may be the substitution of a drug in the same class with the previously prescribed drug because of recent formulary changes. Changing the prescription order may include changing prescription parameters such as the address of the patient.

Figure 5:
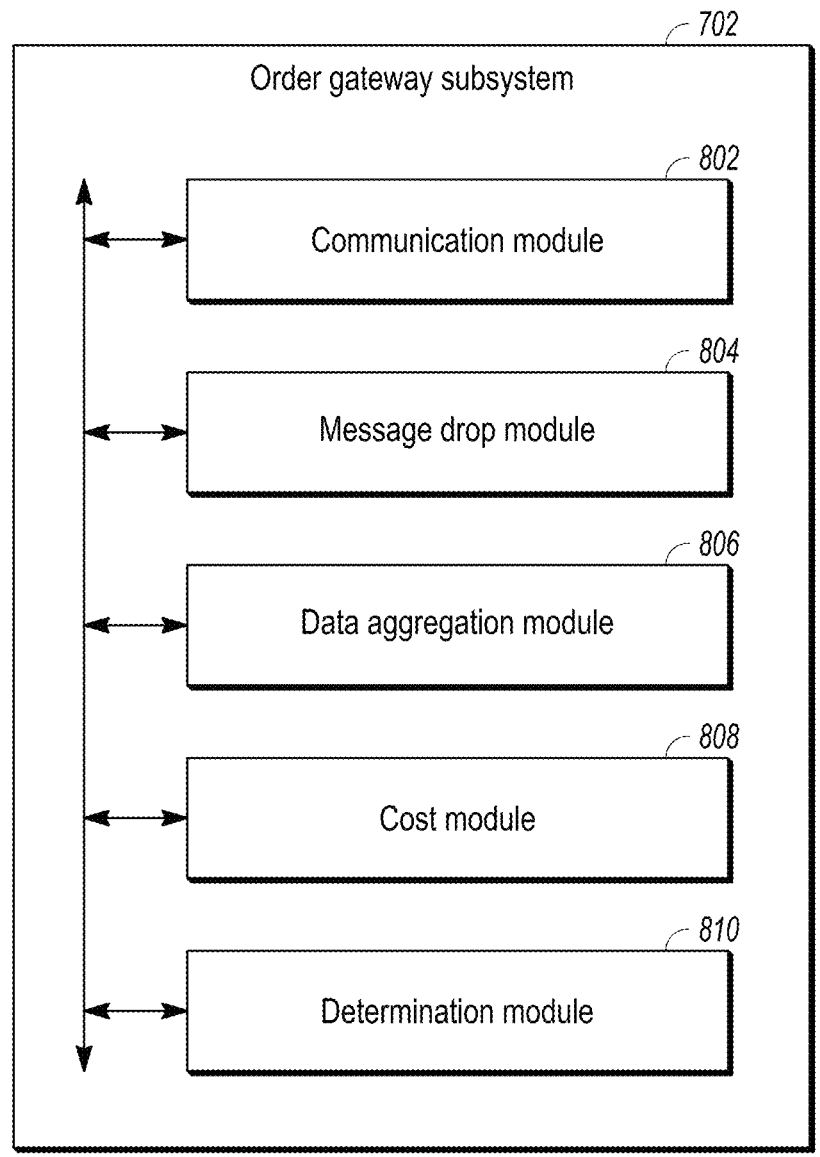
FIG. 5 illustrates one example of an order gateway subsystem.

FIG. 5 illustrates one example of the order gateway subsystem 702. The order gateway subsystem 702 may be deployed in the fulfillment device 612 and/or 614, or may otherwise be used. One or more modules are communicatively coupled and included in the order gateway subsystem 702 to enable communication with the control system 102 and the fulfillment devices 612, 614. The order gateway subsystem 702 may include a communication module 802, a message drop module 804, a data aggregation module 806, a cost module 808, and a determination module 810. In one embodiment, the modules are deployed in memory and executed by a processor or more than one processor coupled to the memory. The functionality contained within the modules 802-810 may be combined into a lesser number of modules, further divided among a greater number of modules, or redistributed among existing modules. Other configurations including the functionality of the modules 802-810 may be used.

The communication module 802 communicatively links the fulfillment device 612 and/or 614 to the network 114. The communication module 802 handles communication of data between two or more data sources using one or more communication protocols such as machine to machine communications and machine to enterprise communications. The message drop module 804 provides storage containment of assigned order messages until they are pulled or downloaded by the fulfillment devices 612, 614. For example, the message drop module 804 utilizes post office protocol (POP) or internet message access protocol (IMAP) for retrieval of the order messages by the fulfillment devices 612, 614. The fulfillment devices 612, 614 may access the message drop module 804 to pull (e.g., download) the order messages assigned to the fulfillment devices 612, 614 at a desired frequency to obtain more prescription orders. In some embodiments, the order gateway subsystem 702 may access the message drop module 804 and push (e.g., send) the message order to the fulfillment devices 612, 614. Furthermore, the order status subsystem 708 may also access the message drop module 804 to change prescription parameters or dispensation preferences in the order message. The order status subsystem 708 may also pause or hold the order message in the message drop module 804, or may cancel or delete the order message in the message drop module 804.

In an example embodiment, the order gateway subsystem 702 contains order messages that are not assigned to a particular fulfillment device 612, 614. The order messages are stored in the message drop module 804 and analyzed by the determination module 810, as explained below.

The order gateway subsystem 702 may include a data aggregation module 806 for aggregating data that includes prescription parameters, dispensation preferences, and dispensary attributes. The data aggregation module 806 may obtain the prescription parameters, dispensation preferences, billing codes, and dispensary attributes from the order processing station, the fulfillment devices 612, 614, the control system 102, and/or from the patient data, the client data, and/or the pharmacy data in the database 114. Dispensation preferences may include implementation of corporate policies, such as inclusion of an envelope for remittance if not enrolled in automatic payment, printing of adherence messages and refill reminders. Dispensation preferences may include one or more patient preferences and/or one or more client preferences. Patient preferences that are relevant during fulfillment of the prescription order may include email notifications, specialty caps on vials, personalized refill reminder messages, personalized adherence messages, or the like. Client preferences that are relevant may include specified shipping containers, mail carriers, specialty labels, brail printing capability, etc. Client preferences may also include the requirement that the prescription be fulfilled at an order fulfillment station that allows unions or utilizes only union mail carriers. Client preferences also include client prioritization. That is, prescription orders from patients of certain clients may have a higher priority for fulfillment than other prescription orders. In other words, an age of the order message may be considered by the fulfillment gateway 106 when determining order fulfillment. The age of the order message is determined by the time of generation of the order message where the order message has not been delivered yet. Dispensary attributes are operational characteristics of the fulfillment devices 612, 614. Examples of dispensary attributes may include: for each fulfillment devices 612, 614, inventory level or availability of prescription drugs; fulfillment of specialty drugs (e.g., compounding); inventory level or availability of specialty containers or caps; marking capability of labels, containers or caps; cost based calculations for the prescribed drugs capable of being fulfilled at the fulfillment devices 612, 614; specialty packaging capability; operational cold rooms; added security for class C-2 narcotic prescription drugs; union-only labor; or the like.

The order gateway subsystem may also include a cost module 808 to calculate cost based calculations for the fulfillment devices 612, 614. The data aggregation module 806 and the cost module 808 may be communicatively coupled and included in the order gateway subsystem to enable site selection. The cost based calculations include a calculated cost-to-fill value associated with each prescription drug at each of the fulfillment devices 612, 614. The cost-to-fill value may be stored as a portion of the pharmacy data and updated by the cost module 808. The cost-to-fill value may be the cost to fulfill a prescribed drug based on costs of labor, shipping, and/or materials, for example, at the fulfillment devices 612, 614. Cost for labor, shipping, and materials may be weighted as desired. Cost of materials may include cost of prescription drugs purchased from distributors, as well as prescription drug containers, caps, packaging supplies, or the like. The cost-to-fill value of the prescription drug may vary among the fulfillment devices 612, 614, (e.g., each fulfillment device 612, 614 having its own, but not necessarily unique, cost-to-fill value per prescription drug). For example, if one of the fulfillment devices 612, 614 is highly automated, it may have a lower cost-to-fill value than another of the fulfillment devices 612, 614. More specifically, if the fulfillment device 612 and/or 614 has an automated process to fulfill a type of prescribed drug in place but another fulfillment device 612 and/or 614 requires manual fulfillment, the cost-to-fill may be lower for automated fulfillment.

The cost based calculations, calculated by the cost module 808, may include a maximum variance value for prescription drugs fulfilled by the fulfillment devices 612, 614. In some embodiments, the maximum variance may be preset and stored in memory. In general, the maximum variance value is a maximum variance in the cost-to-fill value that is tolerable to ensure efficient fulfillment of the prescription order. Fulfillment of the prescription order at the fulfillment devices 612 and/or 614 having a cost-to-fill value greater than the lowest cost-to-fill value among multiple fulfillment devices 612, 614 may be acceptable in some circumstances where the maximum variance value is not exceeded. The maximum variance value is exceeded when the cost-to-fill value of the fulfillment devices 612, 614 is greater than a reference cost-to-fill value (e.g., lowest cost-to-fill value among multiple fulfillment devices 612, 614). An example of a circumstance in which the maximum variance is considered is the case of a backlog at one of the fulfillment devices 612, 614. Another example is when client priority (e.g., age) of the order message, causes the selection of fulfillment device 612 or 614 with a higher cost-to-fill value (that does not exceed the reference cost-to-fill value by the maximum variance value) to ensure timely fulfillment.

The order gateway subsystem 702 may include a determination module 810 that may communicate with the data aggregation module 806 and the cost module 808. The determination module 810 utilizes a rule-based site selection process based on prioritization of the prescription parameters, the dispensation preferences, and the dispensary attributes to determine the appropriate fulfillment device 612, 614 to send the order message. The determination module 810 may update its determination upon a sudden price increase in the prescription drug, a reduction in backlog, a change in formulary, or the like. In such a case, the determination module 810 may access the message drop module 804 to update or refresh the selection among the fulfillment devices 612, 614. The determination module 810 may access the message drop module 804 in the event that the order message needs to be reassigned to a different fulfillment device 612 or 614. That is, the determination module 810 may readdress the order message before it is downloaded by the originally assigned fulfillment device 612, 614.

The determination module 810 may accumulate multiple order messages into a batch for delivery to the fulfillment devices 612, 614. The fulfillment devices 612, 614 may request a specific number of order messages in the batch. That is, the fulfillment devices 612, 614 may identify a desired number of order messages in the batch for delivery. In response, the determination module 810 may accumulate no more order messages than the identified desired number.

In the embodiment in which the order messages are stored in the message drop module 804 without assignment to a particular fulfillment device 612, 614, the determination module 810 may determine which order messages are appropriate for delivery to the fulfillment devices 612, 614. The determination may be based on dispensary attributes, such as cost-to-fill values, dispensation preferences (such as maximum variance values), adjudication responses, etc. In response to the fulfillment devices 612, 614 requesting a batch of multiple order messages, the determination module 810 may determine which order messages have the lowest cost-to-fill values. For example, the dispensary attribute of a fulfillment device 612, 614 may include a cost-to-fill value for Fluoxetine 60 mg that is the lowest of all of the multiple fulfillment devices 612, 614. In this case, order messages associated with prescription orders for Fluoxetine 60 mg are delivered from the message drop module 804 to the fulfillment device 612, 614 with the lowest cost-to fill value.

Regardless of whether the order messages are stored in the message drop module 804 as assigned or unassigned, the order messages may be delivered to the fulfillment devices 612, 614 by pushing or pulling. The fulfillment device 612, 614 may access the message drop module 804 to pull (e.g., download) the order messages assigned to the fulfillment device 612, 614 at a desired frequency to obtain more prescription orders. In some embodiments, the order gateway subsystem 702 may access the message drop module 804 and push (e.g. send) the order message to the fulfillment devices 612, 614. Furthermore, the fulfillment devices 612, 614 may request order messages. Examples of sending the order message without a request may include sending a high priority order message to the fulfillment devices 612, 614 or sending the order message at a preset frequency.

In an example embodiment, the fulfillment device 612, 614 that takes delivery of the order messages is an under capacity fulfillment device 612, 614. Under capacity, as used herein, is intended to impart the real-time existence of a less than desired workload or anticipation of a less than desired work load. The determination module 810 may select order messages based on dispensation preferences, such as maximum variance. Specifically, upon receiving a request for a batch of order messages, the determination module 810 may compare the cost-to-fill value for the prescription drug at the requesting fulfillment device 612, 614 with the maximum variance for the prescription drug. If the cost-to-fill value of the requesting fulfillment device 612, 614 does not exceed the lowest cost-to-fill value (attributed to another fulfillment device 612, 614) by the maximum variance value, the order message for the prescription drug is provided to the requesting fulfillment device 612, 614.

The cost module 808 and/or the determination module 810 may adjust the maximum variance value based on dispensation preferences, such as age of order or client priority, or based on dispensary attributes, such as the loss or substantial incapacitation of a fulfillment device 612, 614. Furthermore, the determination module 810 may determine age of the order message based on the time of generating the order message. That is, the order has been generated following an adjudication response, but not yet delivered to the fulfillment device 612, 614. The time of generating the order message may be a prescription parameter of the order message. The determination module 810 may access dispensation preferences, stored locally or at the database 110, and compare the age of the message order with the dispensation preference. In an example embodiment, the dispensation preference may include an age threshold. The age threshold is a threshold that limits the order message's time in storage at the message drop module 804. If the determination module 810 determines that the order message has aged, starting from the time of generating, past the age threshold, the determination module 810 may communicate with the communication module 802. The communication module 802 may send the order message to a fulfillment device 612, 614 to begin fulfillment. The determination module 810 may also select order messages for delivery to the fulfillment device 612, 614 based on age without consideration of age threshold. For example, older order messages are selected before new order messages.

Figure 6:
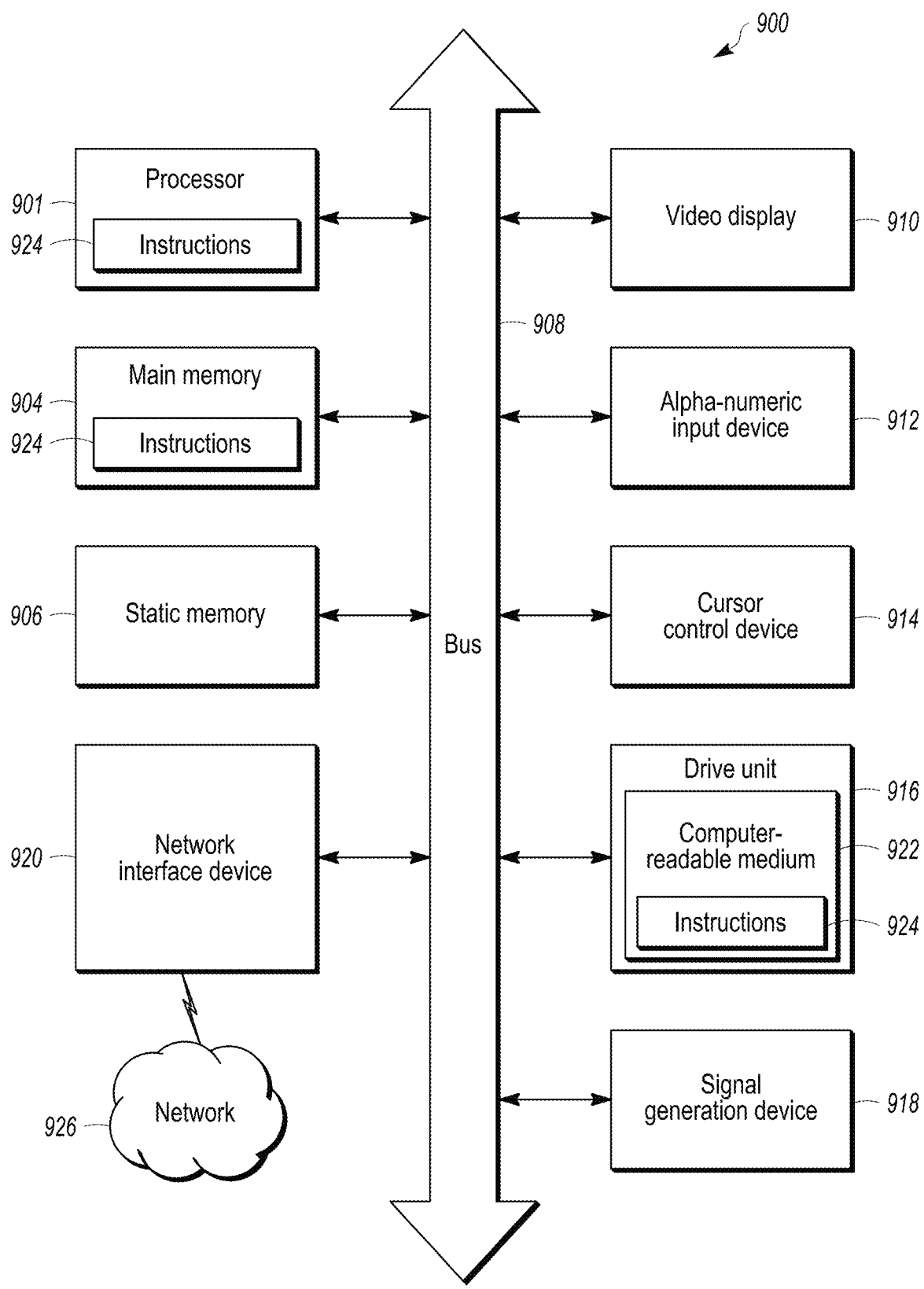
FIG. 6 shows a block diagram of a computer system.

FIG. 6 shows a block diagram of a computer system 900 within which a set of instructions may be executed causing the machine to perform any one or more than one methods, processes, operations, or methodologies discussed herein. For example, the system 900 may represent the control system 102 shown in FIG. 1. The devices 906-930, for example, may include the functionality of the computer system 900. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 900 includes a processor 902 (e.g., a central processing unit (CPU), a graphics processing unit (GPU) or both, etc.), a main memory 904 and a static memory 906, which communicate with each other via a bus 908. The computer system 900 further includes a video display unit 910 (e.g., a liquid crystal display (LCD) or a cathode ray tube (CRT), etc.). The computer system 900 also includes an alphanumeric input device 912 (e.g., a keyboard, etc.), a cursor control device 914 (e.g., a mouse, etc.), a drive unit 916, a signal generation device 918 (e.g., a speaker, etc.) and a network interface device 920.

The drive unit 916 includes a computer readable medium 922 on which is stored one or more than one sets of instructions 924 (e.g., software, etc.) embodying any one or more than one methodologies or functions described herein. The instructions 924 may also reside, completely or at least partially, within the main memory 904 and/or within the processor 902 during execution thereof by the computer system 900, the main memory 904 and the processor 902 also constituting non-transitory computer readable media. When loaded with the instructions 924, the processor 902 is a machine-dedicated to only the present processes and methodologies.

The instructions 924 may further be transmitted or received over a network 926 via the network interface device 920. The instructions can implement multiple communication channels to a provider, e.g., to multiple provider devices and the telehealth control system with one channel being a patient channel that provides data related to the patient and providing connection directly to the patient and a second channel that is a packet channel to provide text messages (e.g., non-video or non-audio communication). The network 926 can represent the network(s) 112 shown in FIG. 1. While the computer-readable medium 922 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The present disclosure uses the term message and/or signal for describing communication over a secondary communication channel to and from the provider devices. In an example embodiment, the message is not an audio signal. In an example embodiment, the message is not a video signal. Messages can be SMS text messages in an example embodiment. The messages can be packets including a header (including sender device and recipient device identification data) and a body of data. The use of a packet for communication on the second channel can allow for the packet to require less bandwidth to route the information to and from the provider device. Routing the packets can use internet protocol (e.g., IPv4, IPv6 and the like) to transmit the packets. The packet replies from the provider device can be a selection reply, e.g., a single character, that in and of itself does not provide any protected or sensitive information and can be interpreted by the telehealth system.

Figure 7:
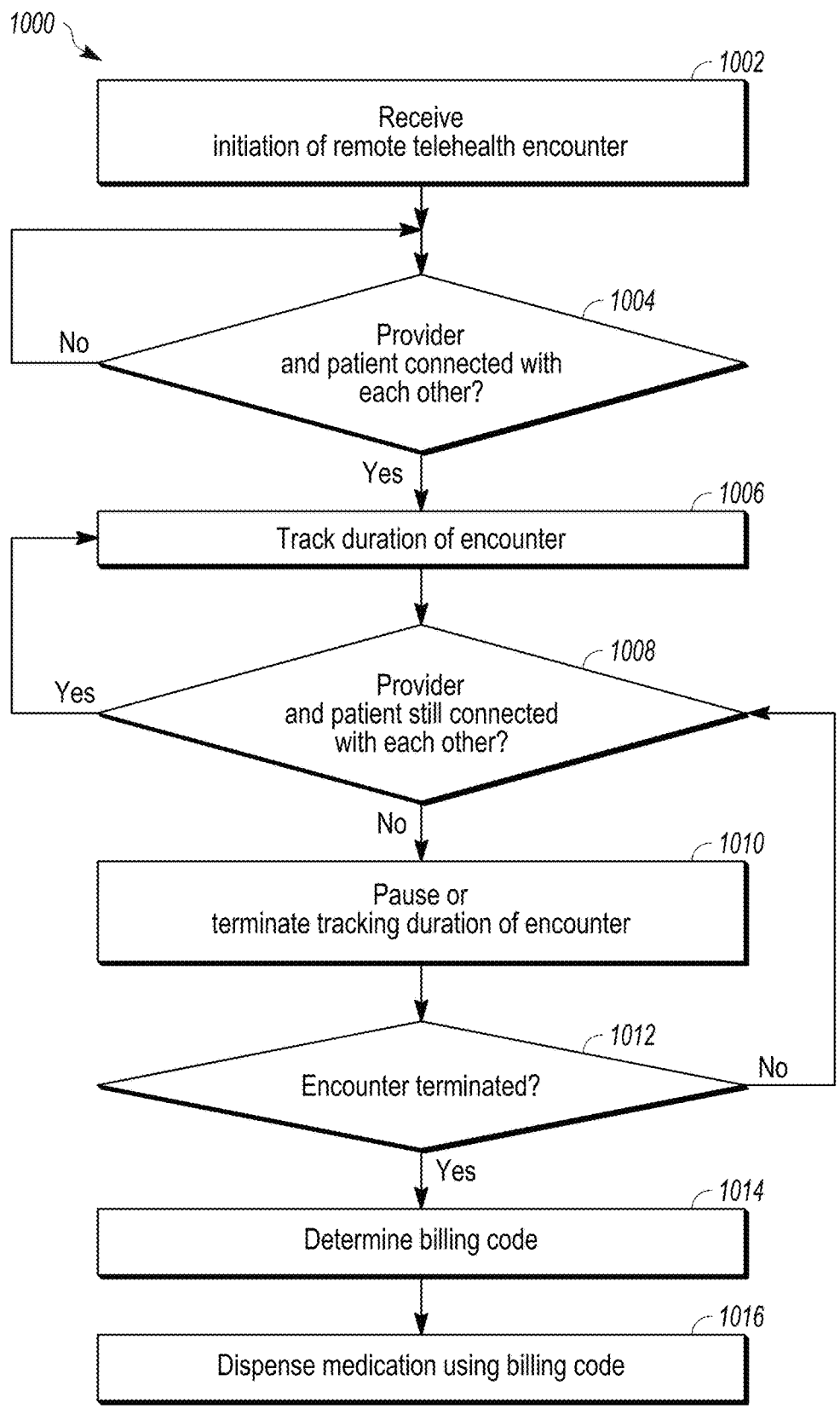
FIG. 7 illustrates a flowchart of one example of a method for tracking a duration of a remote telehealth encounter between a provider and a patient.

FIG. 7 illustrates a flowchart of one example of a method 1000 for tracking a duration of a remote telehealth encounter between a provider and a patient. The method 1000 can represent operations performed by the control system 102, the packaging subsystem 502, the filling system 600, the fulfillment gateway system 700, and/or the order gateway subsystem 702. At step 1002, initiation of a remote telehealth encounter is received. For example, the patient computing device 108, 110 can send a signal to the control system 102 to begin a videoconference and/or teleconference with a provider computing device 104, 106. Alternatively, the provider computing device 104, 106 can send a signal to the control system 102 to begin the videoconference and/or teleconference with the patient computing device 108, 110.

At step 1004, a decision is made as to whether both the provider and patient are concurrently connected to the same encounter. The control system 102 can determine whether the provider computing device 104, 106 and the patient computing device 108, 110 are both connected to the same encounter modality or different encounter modalities. For example, the control system 102 can determine whether both the provider computing device 104, 106 and the patient computing device 108, 110 are able to communicate with each other by being in the same videoconference, by being in the same teleconference, or by otherwise being able to send messages to each other using the telehealth encounter application or website. The control system 102 may monitor messages sent between the provider computing device 104, 106 and the patient computing device 108, 110 to ensure that these devices are able to communicate. If the devices are able to communicate with each other, then the provider and patient are engaged with each other in the telehealth encounter. As a result, flow of the method 1000 can proceed toward step 1006. If the devices are not able to communicate with each other, then the provider and patient may not be engaged with each other in the telehealth encounter. As a result, flow of the method 1000 can stay at step 1004 (or return to 1004) until the provider and patient are in the same telehealth encounter. Alternatively, the method 1000 can terminate.

At step 1006, the duration of the encounter continues to be tracked. That is, the control system 102 can continue to monitor the clock or timer to determine how long the encounter lasts. At step 1008, a decision is made as to whether the provider and the patient are still engaged in the encounter. For example, the control system 102 may determine whether the provider computing device 104, 106 and the patient computing device 108, 110 continue to be connected with each other via the same or different encounter modalities and/or whether a disconnected patient or a disconnected provider has re-connected to the encounter.

If the provider computing device 104, 106 and the patient computing device 108, 110 are not both connected with each other via the same or different encounter modality, then the timing of the duration of the encounter may terminate or be paused. As a result, flow of the method 1000 can proceed toward step 1010. Otherwise, flow of the method 1000 may return to step 1006.

At 1010, timing of the duration of the encounter is paused or terminated. The timing may be paused if one of the provider computing device 104, 106 or the patient computing device 108, 110 is no longer connected with the encounter modality. At 1012, a decision is made as to whether the encounter has ended. The control system 102 can determine whether a termination event has occurred. If a termination event has occurred, then the encounter has ended. As a result, flow of the method 1000 can proceed toward step 1014. If a termination event has not occurred, then the encounter may resume once both the provider and the patient are both connected with each other via the same or different encounter modalities. As a result, flow of the method 1000 can return toward step 1008.

At 1014, the duration of the encounter is used to determine a billing code. Different durations of the encounter may be associated with different billing codes (e.g., in the memory 114). The control system 102 can compare the measured duration of the encounter with the different durations associated with different billing codes to select the billing code associated with the measured duration of the encounter.

At 1016, one or more medications optionally can be dispensed based on or using the billing code that is determined. For example, the billing code can be used by one or more of the packaging subsystem 502, the filling system 600, the fulfillment gateway system 700, and/or the order gateway subsystem 702 to fill one or more containers with a medication that was prescribed by the provider during or subsequent to the encounter. The packaging subsystem 502, the filling system 600, the fulfillment gateway system 700, and/or the order gateway subsystem 702 may require one or more billing codes be provided by the control system 102 to dispense certain medications to the patient involved in the encounter. If the billing code provided by the control system 102 is not a required billing code, then the medication may not be dispensed. If the billing code provided by the control system 102 is a required billing code, then the medication may be dispensed. Flow of the method 1000 may then return to one or more prior steps or may terminate.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware. The modules, controllers and circuitry described herein may include electronic instructions to establish a modality, which is a dedicated machine or circuitry to execute specific tasks as described herein.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP:

Hypertext Preprocessor), Scala, Eiffel, Smalltalk, Erlang, Ruby, Flash®, Visual Basic®, Lua, MATLAB, SIMULINK, and Python®.

None of the elements recited in the claims is intended to be a means-plus-function element within the meaning of 35 U.S.C. § 112(f) unless an element is expressly recited using the phrase "means for," or in the case of a method claim using the phrases "operation for" or "step for."

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

What is claimed is:

1. A method for tracking duration of a remote telehealth encounter between a user computing device and a provider computing device via one or more computer networks, the method comprising:
   receiving, at a telehealth control system, a first signal from at least one of the user computing device or the provider computing device to initiate the remote telehealth encounter via the one or more computer networks;
   identifying a commencement time as when both the user computing device and the provider computing device connect to a same teleconference or videoconference channel via the one or more computer networks to remotely interact with each other in the remote telehealth encounter via the one or more computer networks;
   tracking a duration of the remote telehealth encounter starting at the commencement time while both the user computing device and the provider computing device are connected to each other via the same teleconference or videoconference channel via the one or more computer networks;
   determining whether one of the user computing device or the provider computing device leaves the remote telehealth encounter and disconnects from the same teleconference or videoconference channel via the one or more computer networks while another of the user computing device or the provider computing device remains in the remote telehealth encounter and remains connected to the same teleconference or videoconference channel via the one or more computer networks;
   pausing tracking of the duration of the remote telehealth encounter responsive to determining that one of the user computing device or the provider computing device leaves the remote telehealth encounter and disconnects from the same teleconference or videoconference channel via the one or more computer networks while another of the user computing device or the provider computing device remains in the remote telehealth encounter and remains connected to the same teleconference or videoconference channel via the one or more computer networks;
   resuming tracking of the duration of the remote telehealth encounter responsive to both the user computing device and the provider computing device being connected to each other again by a different channel via the one or more computer networks;
   determining whether the remote telehealth encounter has ended responsive to the user computing device disconnecting from the different channel via the one or more computer networks;
   ending tracking of the duration of the remote telehealth encounter responsive to determining that the remote telehealth encounter has ended;
   determining whether the duration or one or more additional durations that are tracked is longer than a threshold amount of time to ensure that a patient and a provider spent at least the threshold amount of time discussing a medication; and
   controlling the medication packaging subsystem to automatically dispense the medication into a container for the patient by the telehealth control system communicating a second signal or a record to the medication packaging subsystem, the second signal or the record indicating that the patient and the provider spent at least the threshold amount of time discussing the medication, the medication packaging subsystem preventing dispensing of the medication responsive to the patient and the provider not spending at least the threshold amount of time discussing the medication.

2. The method of claim 1, further comprising:
   identifying a billing code based on the duration of the remote telehealth encounter using the telehealth control system having one or more processors that communicate with the medication packaging subsystem, the billing code submitted to one or more of an insurance company or a pharmacy benefit manager for one or more of billing a user or paying a provider that participated in the remote telehealth encounter.

3. The method of claim 1, wherein the different channel is one or more a text message or a short message service (SMS) message.

4. The method of claim 1, wherein resuming tracking of the duration of the remote telehealth encounter occurs responsive to both the user computing device and the provider computing device being connected to each other again via the different channel.

5. A method for tracking duration of a remote telehealth encounter between a user computing device and a provider computing device via one or more computer networks, the method comprising:
   receiving, at a telehealth control system, a first signal from at least one of the user computing device or the provider computing device to initiate the remote telehealth encounter via one or more computer networks;
   beginning to track a duration of the remote telehealth encounter responsive to both the user computing device and the provider computing device connecting to the one or more computer networks to communicate with each other via a first encounter modality;
   determining that the user computing device and the provider computing device are no longer connected to the one or more computer networks for communication with each other via the first encounter modality;
   determining that the user computing device and the provider computing device are re-connected to the one or more computer networks for communication with each other via a second encounter modality that is different from the first encounter modality;

determining whether the remote telehealth encounter has ended after the user computing device and the provider computing device are re-connected to the one or more computer networks to communicate with each other via the second encounter modality;

ending tracking of the duration of the remote telehealth encounter responsive to determining that the remote telehealth encounter has ended with the user computing device or the provider computing device disconnecting from the one or more computer networks;

determining whether the duration of the remote telehealth encounter is at least a threshold amount of time associated with a medication; and sending a second signal or a record from the telehealth control system to the medication packaging system responsive to the duration being at least the threshold amount of time, the second signal or the record controlling the medication packaging system to automatically dispense the medication into a container.

6. The method of claim 5, further comprising:
determining whether both the user computing device and the provider computing device are connected to the first encounter modality to remotely interact with each other in the remote telehealth encounter via the one or more computer networks,
wherein tracking the duration of the remote telehealth encounter occurs responsive to determining that both the user computing device and the provider computing device are connected to the first encounter modality to remotely interact with each other in the remote telehealth encounter via the one or more computer networks.

7. The method of claim 5, further comprising:
determining whether one of the user computing device or the provider computing device disconnects from the one or more computer networks and leaves the remote telehealth encounter while another of the user computing device or the provider computing device remains connected to the one or more computer networks and remains in the remote telehealth encounter; and
pausing tracking of the duration of the remote telehealth encounter responsive to determining that one of the user computing device or the provider computing device disconnects from the one or more computer networks and leaves the remote telehealth encounter while another of the user computing device or the provider computing device remains connected to the one or more computer networks and remains in the remote telehealth encounter.

8. The method of claim 7, further comprising:
resuming tracking of the duration of the remote telehealth encounter responsive to both the user computing device and the provider computing device re-connecting to the one or more computer networks and being connected to each other again via the second encounter modality.

9. The method of claim 7, further comprising:
resuming tracking of the duration of the remote telehealth encounter responsive to both the user computing device and the provider computing device re-connecting to the one or more computer networks and being connected to each other again in the remote telehealth encounter with one of the user computing device or the provider computing device connected to the one or more computer networks and to the remote telehealth encounter via the first encounter modality and another of the user computing device or the provider computing device connected to the one or more computer networks and to the remote telehealth encounter via the second encounter modality.

10. The method of claim 5, further comprising:
identifying and submitting a billing code to one or more of an insurance company or a pharmacy benefit manager for one or more of billing a user or paying a provider that participated in the remote telehealth encounter based on the duration.

11. The method of claim 5, wherein the first encounter modality is one or more of a videoconference or a teleconference, and the second encounter modality is text messages or simple message service (SMS) messages.

12. A tangible and non-transitory computer readable medium comprising instructions that direct one or more processors to:
receive a first signal from at least one of a user computing device or a provider computing device to initiate a remote telehealth encounter via one or more computer networks;
determine whether both the user computing device and the provider computing device are connected to a first encounter modality to remotely interact with each other in the remote telehealth encounter via the one or more computer networks;
track a duration of the remote telehealth encounter that begins with both the user computing device and the provider computing device connecting to the one or more computer networks and connecting with each other via the first encounter modality;
determine whether one of the user computing device or the provider computing device disconnects from the one or more computer networks and leaves the remote telehealth encounter while another of the user computing device or the provider computing device remains connected to the one or more computer networks and remains in the remote telehealth encounter;
pause tracking of the duration of the remote telehealth encounter responsive to determining that one of the user computing device or the provider computing device disconnects from the one or more computer networks and leaves the remote telehealth encounter while another of the user computing device or the provider computing device remains connected to the one or more computer networks and remains in the remote telehealth encounter;
resume tracking of the duration of the remote telehealth encounter responsive to both the user computing device and the provider computing device connecting to the one or more computer networks and connecting to each other again via a second encounter modality that is different from the first encounter modality;
determine whether the remote telehealth encounter has ended by the user computing device and the provider computing device disconnecting from the one or more computer networks;
end tracking of the duration of the remote telehealth encounter responsive to determining that the remote telehealth encounter has ended by the user computing device and the provider computing device disconnecting from the one or more computer networks;
comparing the duration of the remote telehealth encounter with a threshold period of time that is associated with a medication requiring a discussion between a patient and a provider that lasts at least as long as the threshold period of time; and (a) preventing dispensing of a medication to the patient responsive to the duration being shorter than the threshold period of time or (b) dispensing the medication to the patient responsive to the duration being at least as long as the threshold period of time.

13. The tangible and non-transitory computer readable medium of claim 12, wherein the instructions direct the one or more processors to select a billing code based on the duration and submit the billing code to one or more of an insurance company or a pharmacy benefit manager for one or more of billing the patient or paying the provider that participated in the remote telehealth encounter.

14. The tangible and non-transitory computer readable medium of claim 12, wherein the first encounter modality is one or more of a videoconference or a teleconference, and the second encounter modality is text messages or simple message service (SMS) messages.

15. The tangible and non-transitory computer readable medium of claim 12, wherein the instructions direct the one or more processors to resume tracking of the duration of the remote telehealth encounter occurs responsive to both the user computing device and the provider computing device being connected to each other again in the remote telehealth encounter with one of the user computing device or the provider computing device connected to the remote telehealth encounter via one of the first encounter modality or the second encounter modality and another of the user computing device or the provider computing device connected to the remote telehealth encounter via another of the first encounter modality or the second encounter modality.

16. The method of claim 1, further comprising:
preventing the medication packaging subsystem from dispensing another medication into another container for the patient by the telehealth control system communicating a third signal to the medication packaging system responsive to determining that the duration of the remote telehealth encounter is not at least a the threshold amount of time.

17. The method of claim 5, further comprising:
preventing the medication packaging subsystem from dispensing another medication into another container for a patient by the telehealth control system communicating a third signal to the medication packaging system responsive to determining that the duration of the remote telehealth encounter is not at least the threshold amount of time.

* * * * *